United States Patent [19]

Cromartie

[11] Patent Number: 4,940,045
[45] Date of Patent: Jul. 10, 1990

[54] KNEE GUARD AND BRACE WITH ADJUSTABLE MEDIAL CONDYLE SUPPORT PAD

[76] Inventor: Hendrick L. Cromartie, 2 Ridgewood Rd., Rome, Ga. 30161

[21] Appl. No.: 288,637

[22] Filed: Dec. 22, 1988

[51] Int. Cl.⁵ .............................................. A61F 5/00
[52] U.S. Cl. ................................. 128/80 C; 128/80 F
[58] Field of Search ...................... 128/80 C, 80 F, 88, 128/91 A

[56] References Cited

U.S. PATENT DOCUMENTS

| | | | |
|---|---|---|---|
| 3,853,123 | 12/1974 | Moore | 128/80 C |
| 4,144,592 | 3/1979 | Larson | 128/80 C |
| 4,271,831 | 6/1981 | Deibert | 128/80 C |
| 4,372,298 | 2/1983 | Lerman | 128/80 C |
| 4,506,661 | 3/1985 | Foster | 128/80 C |
| 4,556,053 | 12/1985 | Irons | 128/88 |
| 4,602,627 | 7/1986 | Vito et al. | 128/80 F |
| 4,781,179 | 11/1988 | Colbert | 128/80 C |
| 4,781,180 | 11/1988 | Solomonow | 128/80 C |
| 4,793,333 | 12/1988 | Marguette | 128/80 C |
| 4,796,610 | 1/1989 | Cromartie | 128/88 |

Primary Examiner—Edgar S. Burr
Assistant Examiner—Huong Q. Pham
Attorney, Agent, or Firm—Vivian L. Steadman

[57] ABSTRACT

A knee guard and brace having both lateral and medial side members in which a single, medial condyle support pad is affixed to a plate hingedly connected to the inner side of an upper longitudinal rib within the medial side member. A spacer mounted on the plate and rotatable about a pivot thereon determines the angle at which the longitudinal centerlines of the medial condyle support pad and of the upper rib are inclined with respect to each other when the pad is pressed as far as possible medially, that is, in a direction toward the median plane of the human body. The spacer includes an eccentric arm with a ramp which can be rotated about the pivot. The medial condyle support pad is readily positioned to accommodate a particular user without elaborate custom-fitting once the thigh and calf support pads in the lateral side member have been custom-fitted to his leg and strapped thereon. Optimum placement of the medial condyle support pad so as to protect a wearer's knee against valgus-directed forces is achieved simply by pressing the condyle support pad against the inner surface of the knee and rotating the eccentric arm as far as possible into a gap which exists between the plate and the rib and then fixing the arm in that position.

4 Claims, 2 Drawing Sheets

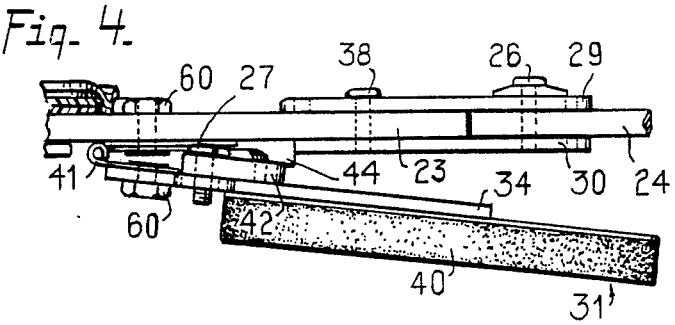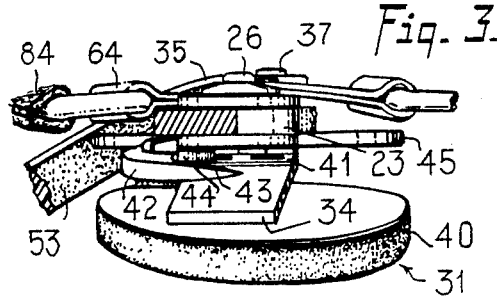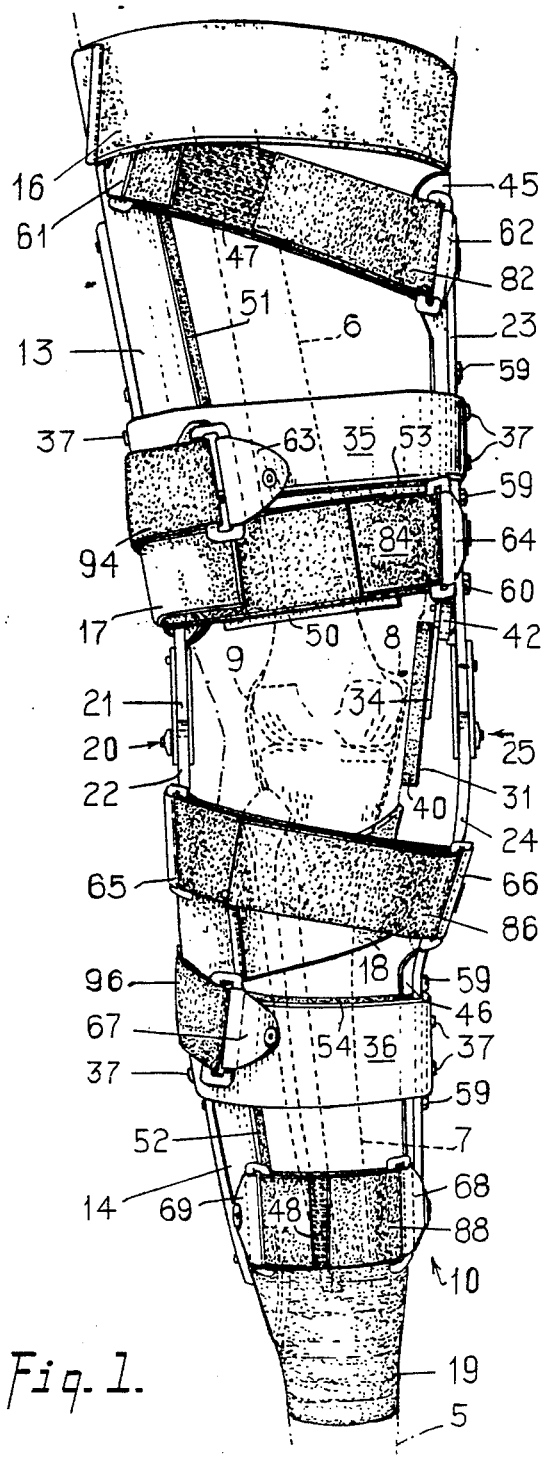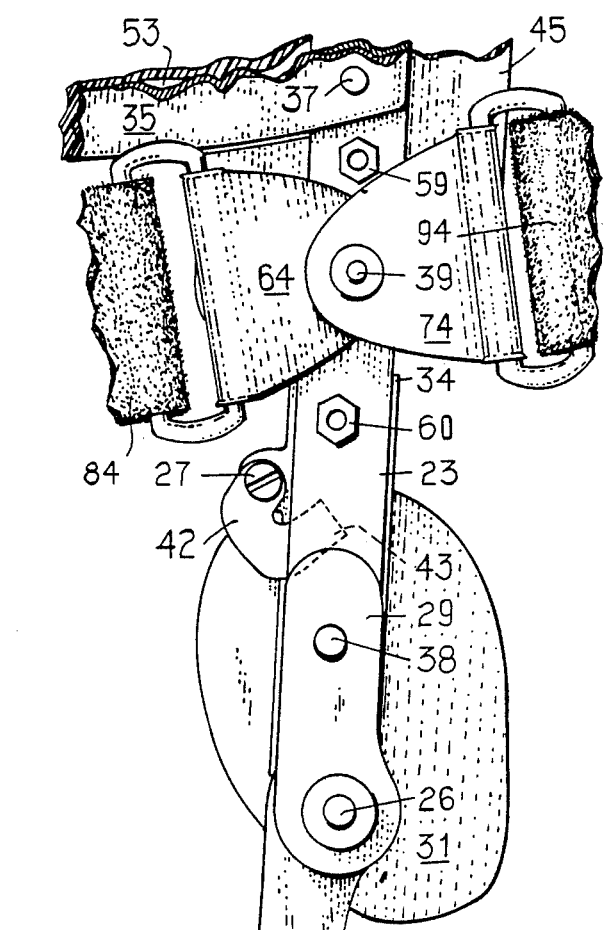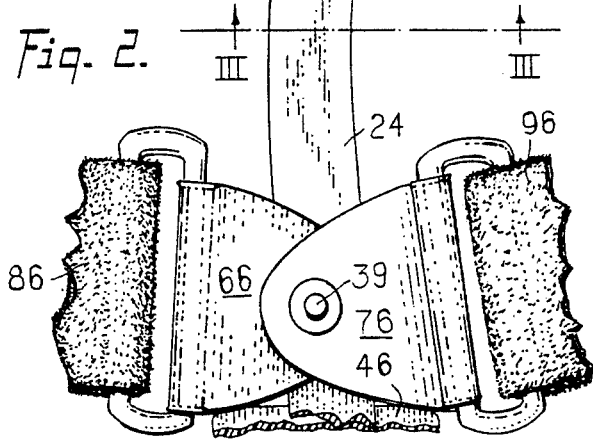

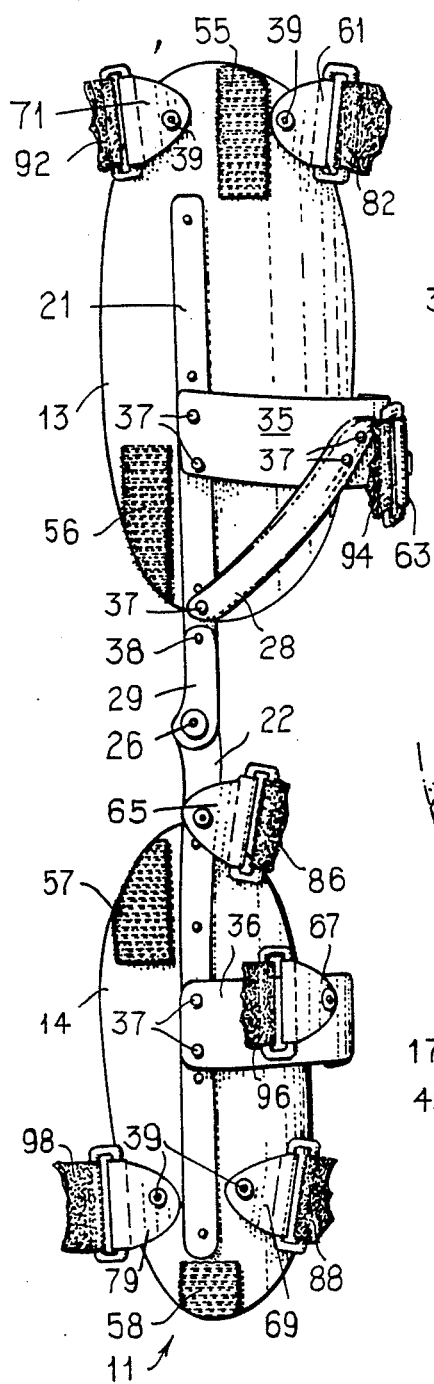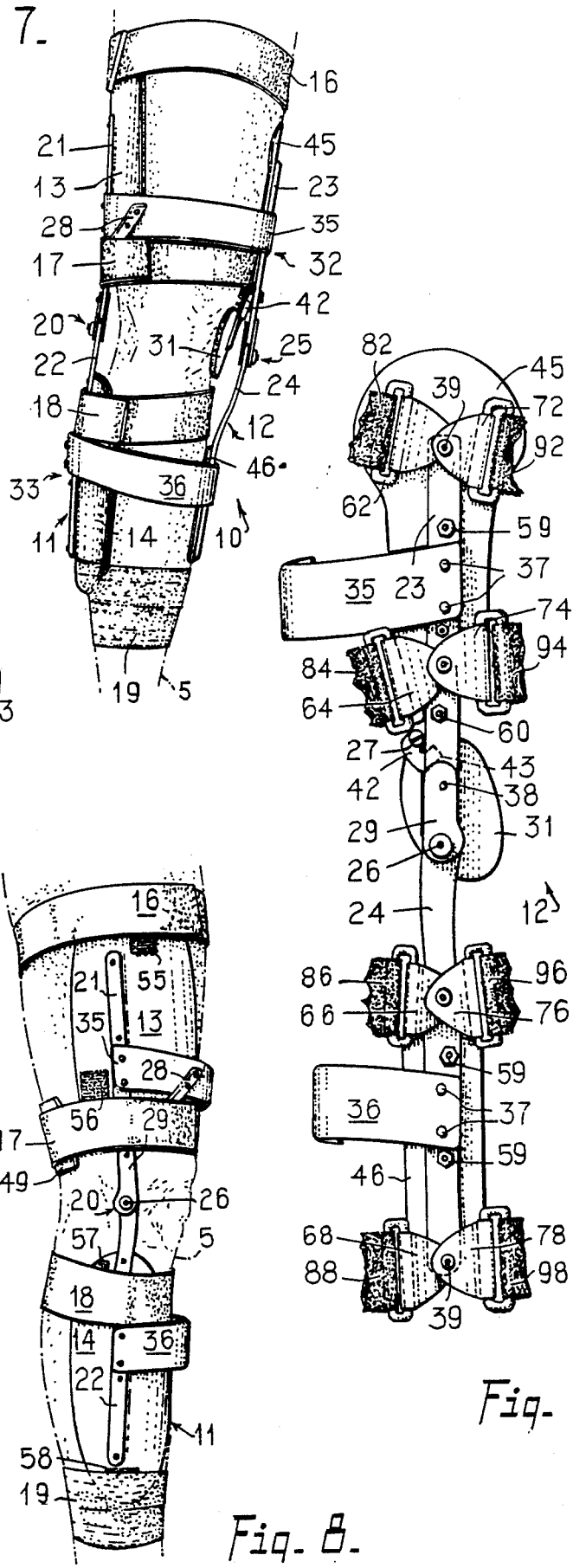

KNEE GUARD AND BRACE WITH ADJUSTABLE MEDIAL CONDYLE SUPPORT PAD

BACKGROUND OF THE INVENTION

1. Field of the Invention

This invention relates generally to a knee guard and brace having both lateral and medial side members in which at least one of these side members has a pair of thigh and calf support pads which is secured to a user's leg by straps and in which a condyle support pad is mounted on at least one of the side members. More particularly, it relates to such a knee guard and brace in which the condyle support pad can move inwardly while the proximate side member remains fixed in position. The invention has specific application in reducing the chance of injury and the extent of damage to the knee area which might otherwise be sustained by an athlete, especially by a football player such as a quarterback when he is tackled in a passing position, and is effective in achieving such reduction whether impact loads are applied to the front, back, or either side of the athlete's leg.

2. Description of the Prior Art

Knee guards and braces with both lateral and medial side members in which condyle support pads are mounted on both side members are known in the prior art. When a knee joint is pushed or bows inwardly under the influence of non-contact forces such as those due to a trick knee, a medial condyle support pad resists medial movement of the knee joint reducing its chance of collapse. Similarly, a lateral condyle support pad resists lateral movement of a knee joint acted upon by varus-directed forces. For each condyle support pad, its effectiveness in resisting such sideways movement is critically dependent upon the position of the pad. That is to say, such a pad is most effective when the pad lies in passive contact with the knee itself. In spite of this fact, none of the prior art devices provides means for adjusting the position of a condyle support pad independently of the remainder of the knee guard and brace.

The difficulties in positioning a medial condyle support pad in a knee guard and brace of the prior art become apparent when one realizes that the orientation of the condyle support pad relative to the medial-lateral plane, a plane which is disposed perpendicular to the median plane of the human body, is of critical importance. Even though the brace may be custom-fitted, the optimum medial-lateral orientation of the condyle support pad varies in relationship to the firmness of the leg when the brace is strapped to the outside surface of the leg. This optimum orientation also varies as the leg changes size during rehabilitation after injury.

Positioning a lateral condyle support pad, on the other hand, presents greater, even insurmountable difficulties. Once a lateral condyle support pad is positioned in contact with the knee joint to resist any lateral movement thereof, the very proximity of the pad to the knee virtually insures that the impact of a lateral blow upon the knee guard and brace is sustained by the knee joint itself.

SUMMARY OF THE INVENTION

In accordance with the present invention, there is provided a knee guard and brace having both lateral and medial side members in which a single, medial condyle support pad is affixed to a plate hingedly connected to an upper longitudinal rib within the medial side member. To facilitate the proper positioning of the medial condyle support pad relative to the medial-lateral plane, there is provided a spacer mounted on the plate and rotatable about a pivot thereon. The position of the spacer determines how close the free end of the plate holding the medial condyle support pad can approach the remainder of the medial side member when the pad is being pressed toward the joint interconnecting the ribs in the medial side member. Hence, the position of the spacer determines the minimum angle at which the longitudinal centerlines of the medial condyle support pad and of the upper rib can be inclined with respect to each other. The spacer, which includes an eccentric arm with a ramp, can be rotated about the pivot until the outer surface of the ramp barely touches the contiguous surface of a protrusion on the upper longitudinal rib. Optimum placement of the medial condyle support pad so as to protect a wearer's knee against valgus-directed forces is achieved by pressing the medial condyle support pad against the inner surface of the knee, then rotating the spacer as far as possible into a gap which exists between the plate and the rib, and finally fixing the spacer in that position.

The improved knee guard and brace further comprises two cross members situated on either side of the knee joint to connect together the lateral and medial side members. Each cross member is rigidly joined to one of two pivotally interconnected longitudinal ribs within each of the side members and arches forwardly, spanning a front portion of the wearer's leg to form, with the two ribs, a cage-like frame. Two frames which are so formed above and below the knee resist both medial and lateral deformations of the pair of longitudinal ribs in the lateral side member and of a mechanical joint structure which interconnects them. As a consequence, even though the ribs in the lateral side member are rigidly fixed to non-yielding thigh and calf support pads, these pads can be extended into close proximity of a wearer's knee joint, thereby positioning the proximal sections of the thigh and calf support pads to protect the knee joint against varus-directed forces while keeping the knee guard and brace out of contact with the knee itself. Any requirement for a lateral condyle support pad is thus obviated as well as the possibility of injury due to such a pad moving medially.

Elastic straps of narrow width attached to the thigh and calf support pads of the lateral side member are used to suspend the two frames at three widely separated points along a wearer's leg. A fourth suspension point for the two frames is provided by taping the calf support pad to the bony structure below the large calf muscles of a wearer's leg. The tape thus anchored to the leg also serves to prevent the knee guard and brace from sliding down during use. Only three of the narrow, elastic straps are utilized, with two of the straps being attached to the ends of the thigh support pad and the third strap to the end of the calf support pad proximate the knee. Wide separation between the points of attachment for the tape and straps is achieved by using thigh and calf support pads of exceptional length and, with the elasticity of the straps, allows a high degree of freedom of movement for the large muscles of the wearer's leg.

Further, the elastic strap and the tape securing the distal ends of the thigh and calf support pads, respectively, interact with the ends of these pads proximal the knee joint to resist varus-directed forces acting on the knee. Similarly, the elastic straps securing the ends of the thigh and calf support pads proximal the knee joint to the wearer's leg interact with the ends of these pads distal the knee joint to resist moderate valgus-directed forces brought to bear on the knee joint. Because the elastic straps proximate the knee keep the proximal portions of the femur and tibia taut against the lateral support pads through all degrees of flexion and extension, the elastic straps are more effective in resisting valgus-directed forces of moderate magnitude than is the condyle support pad. On the other hand, when valgus-directed forces are severe enough to stretch the elastic straps proximal the knee joint, the medial condyle support pad, once it is properly positioned with the use of the spacer, effectively resists inward bowing of the knee and thereby supports the medial collateral ligament.

In addition, auxiliary non-elastic straps variously attached to the lateral and medial side members and to the two cross members are provided to resist traumatic forces acting on the wearer's knee or leg capable of causing anterior or posterior translocation of the tibia or of either tibial condyle or hyperextension of the knee joint.

Thus the present invention provides a knee guard and brace which can be used by athletes participating in contact sports to protect themselves not only from lateral blows to the knee but also from impact loads to the front or back of the leg and to reduce the likelihood of injury to the ligaments of the knee joint from non-contact forces acting on it in either a valgus, a varus, an anterior, or a posterior direction.

A further object of this invention is to provide a strong supportive and protective apparatus for use by orthopedic patients in need of knee or leg bracing.

Other objects and advantages will appear from the following description of an example of the invention, when considered in connection with the accompanying drawing, and the novel features will be particularly pointed out in the appended claims.

BRIEF DESCRIPTION OF THE DRAWING

Further details are explained below with the help of the examples illustrated in the attached drawings in which:

FIG. 1 is a frontal elevational view of a knee guard and brace according to the present invention in which the knee guard and brace is shown strapped to a wearer's right leg;

FIG. 2 is an enlarged fragmentary section of the medial side member in the knee guard and brace according to FIG. 1 showing a frontal elevational view of a spacer mounted on a plate hingedly connected to the upper rib of the medial side member;

FIG. 3 is a cross-section III—III from FIG. 2;

FIG. 4 is an enlarged fragmentary section of the medial side member in the knee guard and brace according to FIG. 1 showing a side elevational view of the spacer;

FIGS. 5 and 6 are side elevational views of fragmentary sections of the knee guard and brace according to FIG. 1 showing the lateral and medial side members, respectively; and FIGS. 7 and 8 are frontal and side elevational views on a reduced scale of the knee guard and brace according to FIG. 1 in which only those straps securing the lateral side member to the wearer's leg are illustrated, the knee guard and brace being shown without any of the keepers for securing the auxiliary straps which are not shown.

Like reference characters indicate corresponding parts throughout the several views of the drawings.

DESCRIPTION OF THE PREFERRED EMBODIMENT

The present knee guard and brace is designed to protect the ligaments of the human knee joint including the medial and lateral collateral ligaments, indicated generally by the reference numerals 8 and 9, respectively, and the anterior cruciate and posterior cruciate ligaments. The ligaments are required to restrict the movements of the knee joint to practically one plane while the axis around which the articulating surfaces move shifts its position slightly during flextion and extension of the joint.

Referring now to the drawings, the present knee guard and brace 10 is shown secured by straps 16, 17, 18 and tape 19 to the right leg 5 of a wearer. As shown in FIGS. 1 and 7, the knee guard and brace 10 comprises a lateral side member 11 and a medial side member 12, each having a pair of longitudinal ribs 21, 22; 23, 24, respectively. In addition, a pair of elongated thigh and calf support pads 13, 14 are rigidly connected by rivets or the like to the distal ends of the ribs 21, 22. Mechanical joint structures 20, 25 interconnect the proximal ends of the ribs 21, 22; 23, 24. The structure 20 and the ribs 21, 22 form a bridge which spans the lateral side of the knee joint; and the structure 25 and the ribs 23, 24 together span the medial side thereof. Neither mechanical joint structure 20, 25 is designed to contact the knee joint whether the wearer's leg is fully extended or flexed; but a single, medial condyle support pad 31 described hereinbelow is adapted to make such contact.

In the preferred embodiment, each of the joint structures 20, 25 includes a pair of joint elements 29, 30 between which are sandwiched the proximal ends of the ribs 21, 22; 23, 24. Each rib 21, 23 is rigidly fixed to one of the pairs of joint elements 29, 30 by a rivet 38; and the rib 22, 24 is pivotally interconnected by a pin 26 to the same pair of joint elements 29, 30 as that to which the rib 21, 23, respectively, is fixed. Other joint structures designed to simulate closely the natural movement of the human knee joint such as those disclosed in U.S. Pat. No. 4,320,747 can obviously be substituted for the structures 20, 25; and such changes are not excluded from the content of this disclosure.

Atop the midsection of each rib 21, 23; 22, 24 is rigidly attached a cross member 35, 36, respectively. Each cross member 35, 36 extends transversely of the longitudinal centerlines of the ribs contiguous with the cross members and forms with them cage-like frames 32, 33. The length and curvature of each cross member 35, 36 is preferably determined by construction of the knee guard and brace 10 from a cast of a wearer's leg. Rivets 37 secure the cross members 35, 36 to the ribs 21, 23; 22, 24 as well as a tie 28 to the rib 21 and the cross member 35. The tie 28, rib 21 and the cross member 35 form a three-sided, pinned structure of exceptional strength. The ribs 21, 22, 23, 24; the joint structures 20, 25; the cross members 35, 36; and the tie 28 are preferably formed of a suitable high strength, lightweight material such as a plastic or non-corrosive metal alloy. In the preferred embodiment, the ribs 21, 22, 23, 24 are fabricated from an aluminum alloy and have a transverse cross-section measuring, by way of example, approximately $\frac{3}{8}$ inch by 3/16 inch.

Each of the frames 32, 33 resists any medial deformation of the ribs 21, 22 even under the impact of a severe lateral blow either to the ribs or to the joint structure 20. As a consequence, the proximal sections of the thigh and calf support pads 13, 14, even though they extend into close proximity of the knee joint, do so without subjecting the knee to potential trauma from any movement in a medial direction on their part when a lateral blow impacts upon either them, the ribs 21, 22 or the joint structure 20.

Elastic straps 16, 17, 18 of narrow width attached to the thigh and calf support pads 13, 14 of the lateral side member 11 are used to suspend the two frames 32, 33 at three widely separated points along a wearer's leg (FIGS. 7 and 8). Tape 19 wrapped about the distal end of the calf support pad 14 below the large leg muscles provides a fourth suspension point for the frames 32, 33. Wide separation between the points of attachment of the tape 19 and of the straps 16, 17, 18 as well as the elasticity of the straps allows a high degree of freedom of movement of the large muscles of the wearer's leg. Importantly, each of the four suspension points for the knee guard and brace 10 can be adjusted independently of the others to give the support required for a particular type of knee deficiency.

The proximal sections of the thigh and calf support pads 13, 14 not only do not transmit the impact of lateral blows upon the device 10 to the knee but, together with the strap 16 and the tape 19, protect the knee joint against forces acting in a varus direction. When such forces act, tending to bow the knee outwardly, the proximal sections of the thigh and calf support pads 13, 14 prevent the heads of the tibia 7 and of the femur 6 from moving in a lateral direction while the strap 16 and the tape 19 simultaneously hold the distal sections of the side member 11 against the thigh and calf, respectively. The elongated thigh and calf support pads 13, 14 provide lever arms of exceptional length for the strap 16 and the tape 19 to act upon as they resist varus-directed forces trying to push the heads of the tibia and of the femur outwardly between the proximal ends of these pads.

In the preferred embodiment, the strap 16 is fabricated of an elasticized material which allows the strap to give slightly as the leg is alternately flexed and extended while maintaining pressure on the femur 6 to hold it against the thigh support pad 13. The tape 19 holds the knee guard and brace 10 in place so it cannot slip along the leg. Because of the downward extension of the pad 14, its distal end can be anchored, using the tape 19, near the bony structure of the leg below the large muscles of the calf (FIG. 1).

To protect the knee joint against moderate forces acting in a valgus direction, on the other hand, there are provided straps 17, 18 attached to the ends of the thigh and calf support pads 13, 14 proximate the knee to secure them to a wearer's leg. Like the strap 16, the straps 17, 18 are preferably fabricated of an elasticized material. Such construction is important in that it not only keeps the sections of the femur 6 and of the tibia 7 proximate the knee taut against the lateral support pads 13, 14, respectively, through all degrees of flection and of extension but also permits freedom of movement of the large muscles of the wearer's leg. When valgus-directed forces act, tending to bow the knee inwardly, the straps 17, 18 hold the proximal sections of the femur 6 and of the tibia 7 against the thigh and calf support pads 13 and 14, respectively, while the distal sections of these pads supply the necessary reciprocating forces.

Valgus-directed forces severe enough to stretch the elastic straps 17, 18 are obviated by the use of a medial condyle support pad 31 which limits the medial movement of the knee. The pad 31 has sufficient length to contact both the medial surfaces of the epi-condyle of the femur 6 and of the head of the tibia 7 so that when the pad is properly positioned it, together with distal portions of the thigh and calf support pads 13, 14, afford four point suspension protection to a wearer's knee joint, thereby preventing any tearing of the ligaments of the knee or shearing between the heads of the tibia and of the femur when severe valgus-directed forces act.

As is best seen in FIGS. 3 and 4, the condyle support pad 31 is affixed to a plate 34 which is connected by a hinge 41 to the upper longitudinal rib 23 within the medial side member 12. Preferably formed of stainless steel or the like, the hinge is attached to the plate 34 and to the rib 23 by fasteners such as the bolts and nuts 60. The hinge 41 allows the pad 31 to assume a variety of orientations with respect to the rib 23 and is attached to the rib above the knee so that the pad 31 slopes downwardly and laterally as do the medial surfaces of the knee generally (FIG. 1). The wide range through which the angle between the longitudinal centerlines of the rib 23 and of the pad 31 can vary facilitates fitting the pad 31 to a wearer's knee. This ease of fitting exists even though the pad extends substantially the lengths of the heads of the femur 6 and of the tibia 7 and the orientations of the medial side member 12 and of the medial surfaces of the knee fluctuate markedly, varying with a wearer's muscle tone, body fat content, and change in leg size during rehabilitation following injury.

The travel of the end of the plate 34 distal the hinge 41 in a medial direction is limited by a spacer 42 mounted on the plate 34 and rotatable about a pivot pin 27 thereon. The position of the spacer 42 determines how close the plate holding the pad 31 can approach the remainder of the medial side member 12 when the pad is being pressed thereagainst. The spacer 42 which includes an eccentric arm with a ramp 43 can be rotated about the pin 27 until the outer surface of the ramp barely touches the contiguous surface of a protrusion 44 on the rib 23. Optimum placement of the pad 31 so as to protect a wearer's knee against severe valgus-directed forces is achieved by pressing the pad 31 against the inner surface of the knee, then rotating the spacer 42 as far as possible into any gap existing between the plate 34 and the rib 23, and finally fixing the spacer in that position. Preferably, the spacer 42 is so fixed when the user's leg is partially flexed.

Four point suspension protection from hyperextension and from anterior and posterior translocation of the tibia and of either tibial condyle is afforded by non-elastic auxiliary straps 82, 92; 84, 94; 86, 96; 88, 98. When the knee joint is acted upon by a force which would tend to hyperextend it, the straps 94, 96 interacting with keepers 63, 74; 67, 76, respectively, prevent the heads of the tibia 7 and of the femur 6 from moving in a posterior direction while straps 82, 88 interacting with keepers 61, 62; 68, 69, respectively, supply the necessary reciprocating force.

When a force acts to translocate the tibia or either tibial condyle in a posterior direction, strap 96 interacting with keepers 67, 76 stabilizes the head of the tibia while straps 92, 88, 84 interacting with keeps 71, 72; 68, 69; 64 and the thigh support pad 13, respectively, supply the necessary reciprocating force. Similarly, when a force acts to translocate the tibia or either tibial condyle in an anterior direction, strap 86 interacting with keepers 65, 66 stabilizes the head of the tibia while straps 82, 94, 98 interacting with keepers 61, 62; 63, 74; 78, 79 supply the necessary reciprocating force.

As is best seen in FIG. 1, each of the support pads 13, 14 includes a rigid outer shell backed by sections of padding 51, 52. The shell is preferably fabricated of a plastic such as polyethylene or the like which measures, by way of example, approximately 0.15 inch in thickness. Each outer shell has curvature in both a transverse and a longitudinal direction to simulate the natural curvature of the limb so that the pads 13 and 14 can accomodate the large muscles of a wearer's thigh and calf, respectively. The surface areas of the pads 13, 14 in contact with a wearer's limb are sufficient to stabilize the device 10 so that it can maintain its correct position on the leg and afford a considerable degree of protection from trauma that might otherwise fracture the fibula, tibia or femur. Moreover, when the device 10 is strapped to the lateral surface of the leg, the compression forces exerted by the straps 16, 17, 18 is spread over a large area, thereby minimizing any pressure points that could lead to skin irritation as the knee guard and brace attempts to follow the motion of the knee as it is alternately flexed and extended.

In addition, shields 45, 46 of similar thickness and material to the shells of the pads 13, 14 but having no padding are secured to the ribs 23, 24 by fasteners such as the bolts and nuts 60. Even though the knee guard and brace 10 is preferably custom-constructed on a cast of a wearer's leg, the extent to which the thigh and calf support pads 13, 14 will compress the leg when the device 10 is strapped to the outside surface of the leg is unknown. Accordingly, one cannot predict whether the ribs 23, 24 will lie passively or fit snugly against the leg or even lie completely out of contact with it. In the event there is a snug fit, the shields 45, 46 prevent the ribs 23, 24 from irritating the skin.

Sections of padding 40, 53, 54, similar in material and thickness to the padding 51, 52 also back the pad 31 and the cross members 26, 27. Like the cross members 26, 27, the plate 34 and the thin outer shell of the pad 31 are preferably fabricated from a suitable high strength, lightweight material such as an aluminum alloy to give them strength to resist severe valgus-directed forces.

Faces 55, 56, 57, 58 of Velcro TM-type cloth fasteners are attached to the pads 13, 14; strips of material (not shown) which mesh with these faces to complete a cloth fastener are stitched to the inner surfaces of the straps 16, 17, 18 proximate an end of each so that they can be secured to the pads 13, 14. The straps 16, 17, 18 also have faces (not shown) similar to the faces affixed to the pads 13, 14 which mesh with inwardly facing strips of material (not shown) on the straps to complete additional cloth fasteners. The latter cloth fasteners are utilized to secure the free end of each strap 16, 18 to itself once the strap has been wrapped about the wearer's leg and to secure the strap 17 both to itself and to a non-elastic strap 84, one end of which is sandwiched between overlapping portions of the straps 17 (FIG. 1).

The strap 84 is one of a plurality of auxiliary straps which connect the side members 11, 12 (FIGS. 1, 5 and 6). In securing non-elastic straps 82, 92, 88, 98, the opposite ends of each strap are passed through keepers 61, 62; 71, 72; 68, 69,; 78, 79, respectively, each of which is attached by a rivet 39 to the device 10. The ends of each strap are then pulled back across the strap itself (FIG. 1). In the process, faces 47, 48 of Velcro TM-type cloth fasteners are brought into contact with strips of material (not shown) with which they can mesh to complete the fastener when the opposite ends of each strap have been pulled sufficiently tight. These strips of meshing material (not shown) are disposed proximate the ends of each strap 82, 92, 88, 98.

Similarly, the opposite ends of each non-elastic strap 94, 86, 96 are passed through keepers 63, 74; 65, 66; 67, 76, respectively, and pulled across the strap; and one end of the strap 84 is likewise secured by a keeper 64 and pulled back across itself. The opposite end of the strap 84, which is sandwiched between portions of the strap 17, is secured thereto by cloth fasteners (not shown). The non-elastic straps, together with the frames 32, 33, protect the knee joint from hyperextension and anterior or posterior translocation of the tibia or of either tibial condyle.

In order to prevent binding, a section of a thin padding 49 formed of fabric may be secured to the strap 17 along a portion thereof which comes into contact with the back of a wearer's leg (FIG. 8). In addition, padding 50 is preferably attached to the inner side of a portion of the non-elastic strap 84 which overlies the strap 17 along a section thereof which contacts the front of a wearer's leg (FIG. 1).

What is claimed is:

1. A knee guard and brace, which comprises:
(a) lateral and medial side members which are adpated to fit on the outer and inner sides, respectively, of a wearer's leg, the lateral side member having first and second ribs and a pair of elongated thigh and calf support pads, the first and second ribs being rigidly connected to the thigh and calf support pads, respectively; the medial side member having third and fourth ribs; an elongated condyle support pad; and means hingedly connected to the third rib for supporting the condyle support pad, the supporting means lacking means for applying a spring-like bias to the condyle support pad, the supporting means including a plate on which the condyle support pad is rigidly mounted;
(b) first means situated generally between the pads for interconnecting the first and second ribs, the first and second ribs and the first interconnecting means forming a lateral bridge over the knee joint;
(c) a thigh cross member which is rigidly connected to the first and third ribs and a calf cross member which is rigidly connected to the second and fourth ribs;
(d) second means situated generally between the thigh and calf cross members for interconnecting the third and fourth ribs, the third and fourth ribs and the second interconnecting means forming a medial bridge over the knee joint;
(e) the thigh cross member and the first and third ribs forming an upper frame and the second and fourth ribs and the calf cross member forming a lower frame, the upper and lower frames preventing the lateral bridge from deforming medially under the impact of a blow;
(f) means for suspending the upper and lower frames along the wearer's leg; and
(g) means mounted on said supporting means for limiting the travel, in a direction toward the second interconnecting means, of an end of the condyle support pad which is distal from points at which said supporting means is hingedly connected to the third rib, the limiting means including means for adjusting the extent to which said end of the condyle support pad can travel in a direction toward the second interconnecting means; the limiting means further comprising means including a spacer rotatable about a pivot on the plate for determining the angle at which the longitudinal centerlines of the condyle support pad and of the third rib can be inclined with respect to each other.

2. The knee guard and brace according to claim 1 wherein the spacer includes an eccentric arm with a ramp which, by rotating the spacer about the pivot, can be positioned so that the ramp protrudes into a gap which exists between the plate and the third rib whenever the condyle support pad is pressed against the knee.

3. A knee guard and brace, which comprises:
  (a) lateral and medial side members which are adapted to fit on the outer and inner sides, respectively, of a wearer's leg, the lateral side member having first and second ribs and a pair of elongated thigh and calf support pads, the first and second ribs being rigidly connected to the thigh and calf support pads, respectively; the medial side member having third and fourth ribs; a cross member rigidly connecting the lateral and medial side members;
  (b) means for securing the thigh and calf support pads to the wearer's leg;
  (c) first means situated generally between the support pads for interconnecting the first and second ribs, the first and second ribs and the first interconnecting means forming a lateral bridge over the knee joint;
  (d) second means for interconnecting the third and fourth ribs, the third and fourth ribs and the second interconnecting means forming a medial bridge over the knee joint;
  (e) a single, unpaired condyle support pad;
  (f) means attached to the inner side of the third rib at points generally above the knee for supporting the condyle support pad in such a way that the condyle support pad can assume a variety of orientation relative to the third rib including those in which the condyle support pad slopes downwardly and laterally as do the medial surfaces of the knee generally, the condyle support pad supporting means including a plate to which the condyle support pad is rigidly attached and a hinge connecting the plate to the third rib; and
  (g) means mounted on the plate and rotatable into a gap which exists between the plate and the third rib whenever the condyle support pad is pressed against the knee for limiting the travel of the condyle support pad in a direction outwardly and toward the second interconnecting means.

4. A knee guard and brace, which comprises:
  (a) lateral and medial side members which are adapted to fit on the outer and inner sides, respectively, of a wearer's leg, the lateral side member having first and second ribs and a pair of elongated thigh and calf support pads, the first and second ribs being rigidly connected to the thigh and calf support pads, respectively; the medial side member having third and fourth ribs; a cross member rigidly connecting the lateral and medial side members;
  (b) means for securing the thigh and calf support pads to the wearer's leg;
  (c) first means situated generally between the support pads for interconnecting the first and second ribs, the first and second ribs and the first interconnecting means forming a lateral bridge over the knee joint;
  (d) second means for interconnecting the third and fourth ribs, the third and fourth ribs and the second interconnecting means forming a medial bridge over the knee joint;
  (e) a single, unpaired condyle support pad; and
  (f) a plate to which the condyle support pad is rigidly attached, a hinge connecting the plate to the third rib, and means mounted on the plate and rotatable into a gap which exists between the plate and the third rib whenever the condyle support pad is pressed against the knee for limiting the travel of the condyle support pad in a direction outwardly and toward the second interconnecting means.

* * * * *